United States Patent [19]
Faden

[11] Patent Number: 5,025,018
[45] Date of Patent: Jun. 18, 1991

[54] CENTRAL NERVOUS SYSTEM INJURY TREATMENT WITH OPIATE-RECEPTOR ANTAGONIST

[75] Inventor: Alan I. Faden, Mill Valley, Calif.

[73] Assignee: Medicis Corporation, New York, N.Y.

[21] Appl. No.: 571,019

[22] Filed: Aug. 22, 1990

Related U.S. Application Data

[63] Continuation of Ser. No. 456,235, Dec. 27, 1989, abandoned, which is a continuation of Ser. No. 287,685, Dec. 20, 1988, abandoned, which is a continuation of Ser. No. 58,340, Jun. 5, 1987, abandoned.

[51] Int. Cl.⁵ .................... A61K 31/435; A61K 31/44
[52] U.S. Cl. ...................................... 514/277; 514/285
[58] Field of Search ................................ 514/277, 285

[56] References Cited

PUBLICATIONS

Chem. Abst.–106–113401G (1987).
Faden et al., "Opiate Antagonist WIN 44,441-3 Stereospecifically Improves Neurologic Recovery after Ischemic Spinal Injury" Neurology, vol. 35, No. 9, pp. 1311–1315, Sep. 1985.
Ward et al., "Multiple Opioid Receptor Profile in Vitro and Activity in Vivo of the Potent Opioid Antagonist WIN 44,441-3", Life Sciences, vol. 33 Sup. I, pp. 303–306, 1983.

Primary Examiner—Stanley J. Friedman
Assistant Examiner—Zohreh A. Fay
Attorney, Agent, or Firm—Jones, Askew & Lunsford

[57] ABSTRACT

The present invention involves methods of inducing opiate-receptor antagonistic activity in a patient suffering from ischemic or traumatic central nervous system injury by administering to said patient an effective amount of an opiate-receptor antagonist having enhanced activity at the kappa-opiate receptor suitable to permit the induction of opiate-receptor antogonistic activity.

6 Claims, No Drawings

CENTRAL NERVOUS SYSTEM INJURY TREATMENT WITH OPIATE-RECEPTOR ANTAGONIST

This is a continuation of application Ser. No. 456,235, filed Dec. 27, 1989, now abandoned, which is a continuation of Ser. No. 287,685, filed Dec. 20, 1988, now abandoned, which is a continuation of Ser. No. 058,340, filed June 5, 1987, now abandoned.

BACKGROUND OF THE INVENTION

Endogenous opioids may be released following traumatic or ischemic injury of the central nervous system. These opioids may serve as secondary pathophysiologic factors contributing to the neurological disorder which stems from the injury to the central nervous system. Opiate receptor antagonists, such as naloxone, have been used to treat brain or spinal cord injury at dosages in the range of 1 to 10 mg/kg of body weight of the patient.

However, naloxone is neither completely selective nor a pure opiate antagonist in all situations. At low dosages, naloxone has considerable selectivity for the mu-opiate receptor. At higher dosages, naloxone acts on other opiate receptors, including the delta and kappa receptors. Further at higher dosages, naloxone may have effects that are not mediated by opiate receptors.

In order to simplify and enhance the safety of central nervous system protocols, opiate receptor antagonists which exhibit a high degree of specificity for or enhanced activity at a specific opiate receptor are being sought. Also, opiate receptor antagonists which act exclusively as such without producing any undesirable side reactions within the body are preferred.

DETAILED DESCRIPTION OF THE INVENTION

The present invention provides a method of inducing opiate-receptor antagonistic activity in a patient suffering from ischemic or traumatic central nervous system injury which comprises administering to said patient an effective amount of an opiate-receptor antagonist having enhanced activity at the kappa-opiate receptor suitable to permit the induction of opiate-receptor antagonistic activity.

As an opiate-receptor antagonist of the present invention there is contemplated any pharmaceutically acceptable compound or salt thereof having enhanced activity at the kappa-opiate receptor capable of inducing opiate receptor antagonistic activity.

As an effective amount of the opiate-receptor antagonist of the present invention there is contemplated an amount of antagonist which is sufficient to induce Kappa opiate receptor antagonistic activity. An effective amount of the opiate receptor antagonist of the present invention is from about 0.01 to about 10 mg/kg body weight of the patient daily. A preferred embodiment of the present invention involves an effective amount of the opiate receptor antagonist from about 0.1 to about 1 mg/kg body weight of the patient daily.

The opiate receptor antagonist of the present invention may be administered to the patient in any dosage form convenient under the patient's specific circumstances. Usually, parenteral administration is preferred.

As a parenteral dosage form there is contemplated a dosage unit suitable for intravenous administration which comprises (i) an effective amount of an opiate receptor antagonist having enhanced activity at or specificity for the kappa opiate receptor and (ii) a pharmaceutically acceptable solution.

As a pharmaceutically acceptable solution there is contemplated any solution which is safe for injection and which is biologically inert and hence does not interfere with the active ingredient. As such a pharmaceutically acceptable solution may be mentioned an isotonic solution suitable for injection into a patient. The isotonic solution may contain water, salt and conventional ingredients such as glucose.

A preferred embodiment of the present invention provides a method of inducing opiate-receptor antagonistic activity in a patient suffering from ischemic or traumatic central nervous system injury, wherein the opiate receptor antagonist administered to the patient is nalmefene. Nalmefene can be obtained in accordance with the method of Hahn et al. (J. Med. Chem. 18:259–262, 1975).

Another preferred embodiment of the present invention provides a method of inducing opiate-receptor antagonistic activity in a patient suffering from ischemic or traumatic central nervous system injury, wherein the opiate receptor antagonist administered to the patient is binaltorphimine. Binaltorphimine can be obtained in accordance with the method of as indicated in Portoghesie et al. (Life Sciences, Vol. 40, pp. 1287–1292, 1987).

An additional preferred embodiment of the present invention provides a method of inducing opiate-receptor antagonistic activity in a patient suffering from ischemic or traumatic central nervous system injury, wherein the opiate receptor antagonist administered to the patient is norbinaltorphimine. Norbinaltorphimine can be prepared in accordance with the method of Lipkowski et al. (Tetrahedion Letters, Vol. 27, pp. 4257–4260, 1986).

The backbone for both binaltorphimine and norbinaltorphinine is as follows.

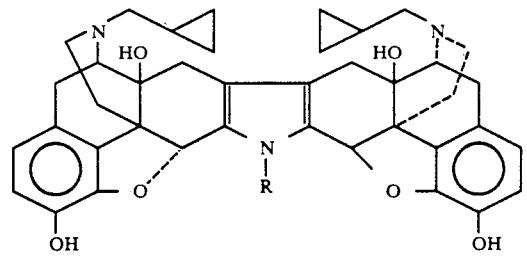

When R is a methyl group, the compound is binaltorphinine. When R is hydrogen, the compound is norbinaltorphinine.

A further preferred embodiment of the present invention provides a method of inducing opiate-receptor antagonistic activity in a patient suffering from ischemic or traumatic central nervous system injury, wherein said opiate-receptor antagonist is administered in a dosage of from about 0.1 mg/kg to about 10 mg/kg 1–3 times daily. A more preferred embodiment of the present invention provides a method of inducing opiate-receptor antagonistic activity in a patient suffering from ischemic or traumatic central nervous system injury, wherein said opiate-receptor antagonist is administered in a dosage of about 0.1 mg/kg 1–3 times daily for nalmefene and about 10 mg/kg 1-3 times daily for binaltorphimine.

The following illustrate the invention.

EXAMPLE 1

Nalmefene is admixed with 10 cc isotonic solution to obtain a final concentration of active ingredient in the solution of 1 mg/cc.

EXAMPLE 2

Binaltorphimine is admixed with 10 cc isotonic solution to obtain a final concentration of active ingredient in the solution of 100 mg/cc.

EXAMPLE 3

Norbinaltorphimine is admixed with 10 cc isotonic solution to obtain a final concentration of active ingredient in the solution of 100 mg/cc.

EXAMPLE 4

Induction of opiate receptor antagonistic activity in a patient suffering from traumatic or ischemic central nervous system injury is accomplished through injection of 0.1 mg/kg of the pharmaceutical preparation of Example 1 2 times daily for 1 day.

EXAMPLE 5

Induction of opiate receptor antagonistic activity in a patient suffering from traumatic or ischemic central nervous system injury is accomplished through injection of 10 mg/kg of the pharmaceutical preparation of Example 2 3 times daily for 1 day.

EXAMPLE 6

Induction of opiate receptor antagonistic activity in a patient suffering from traumatic or ischemic central nervous system injury is accomplished through injection of 10 mg/kg of the pharmaceutical preparation of Example 3 1 time daily for 1 day.

What is claimed is:

1. A method of inducing kappa-opiate-receptor antagonistic activity in a patient suffering from ischemic or traumatic central nervous system injury which comprises administering to said patient an effective amount of a kappa-opiate-receptor antagonist suitable to permit the induction of kappa-opiate receptor antagonistic activity.

2. The method of claim 1, wherein said kappa-opiate-receptor antagonist is nalmefene.

3. A method of treating a patient suffering from ischemic or traumatic central nervous system injury which comprises administering to said patient an effective amount of binaltorphimine suitable to permit the induction of kappa-opiate receptor antagonistic activity.

4. A method of treating a patient suffering from ischemic or traumatic central nervous system injury which comprises administering to said patient an effective amount of norbinaltorphimine suitable to permit the induction of kappa-opiate receptor antagonistic activity.

5. A method of claim 1, wherein said opiate-receptor antagonist is administered in a dosage of from about 0.1 to about 10 mg/kg 1-3 times daily.

6. A method of claim 1, wherein said opiate-receptor antagonist is administered in a dosage of from about 0.1 to about 1.0 mg/kg 1-3 times daily.

* * * * *